_United States Patent_ [19]

Huey et al.

[11] Patent Number: 4,935,173
[45] Date of Patent: Jun. 19, 1990

[54] PROCESS FOR PRODUCING PRILLS

[75] Inventors: A. Michael Huey, Lake Jackson, Tex.; Arthur R. Shirley, Jr.; Phillip A. Forsythe, both of Florence, Ala.

[73] Assignee: The Dow Chemical Company, Midland, Mich.

[21] Appl. No.: 290,716

[22] Filed: Dec. 23, 1988

Related U.S. Application Data

[62] Division of Ser. No. 5,507, Jan. 20, 1987, Pat. No. 4,793,783.

[51] Int. Cl.$^5$ ............................................. B29B 9/10
[52] U.S. Cl. ........................................ 264/14; 425/10
[58] Field of Search ...................... 264/13, 14; 425/10

[56] References Cited

U.S. PATENT DOCUMENTS

| | | | |
|---|---|---|---|
| 440,866 | 4/1984 | Lunghofer et al. | 501/127 |
| 1,033,416 | 7/1912 | Kemp et al. | 239/550 |
| 2,402,192 | 6/1946 | Williams et al. | 23/103 |
| 2,774,660 | 2/1956 | Cook et al. | 71/64 |
| 2,898,625 | 8/1959 | Chao | 425/10 |
| 2,955,807 | 10/1960 | Riley et al. | 257/300 |
| 3,084,914 | 4/1963 | Davis | 165/61 |
| 3,231,413 | 1/1966 | Berquin | 117/100 |
| 3,234,307 | 2/1966 | Tuttle | 264/14 |
| 3,255,036 | 6/1966 | Kramer et al. | 117/100 |
| 3,334,160 | 8/1967 | Wisneski et al. | 425/10 |
| 3,398,191 | 8/1968 | Thompson et aL. | 260/555 |
| 3,556,403 | 1/1971 | Manginelli | 239/135 |
| 3,579,721 | 5/1971 | Kaltenbach | 264/13 |
| 3,711,254 | 1/1973 | McGowan et al. | 23/313 |
| 3,867,410 | 2/1975 | Brand et al. | 260/346.4 |
| 3,869,479 | 3/1975 | Barth et al. | 260/346.4 |
| 3,877,415 | 4/1975 | Blouin | 118/303 |
| 3,991,225 | 11/1976 | Blouin | 427/3 |
| 4,002,198 | 1/1978 | Wagner et al. | 165/61 |
| 4,133,290 | 1/1979 | Melliger | 118/7 |
| 4,190,622 | 2/1980 | Landis | 264/14 |
| 4,213,924 | 7/1980 | Shirley, Jr. | 264/7 |
| 4,252,772 | 2/1981 | Way | 422/244 |
| 4,272,234 | 6/1981 | Tse | 425/222 |
| 4,353,852 | 10/1982 | Tse | 264/37 |
| 4,424,176 | 2/1984 | Shirley, Jr. et al. | 264/7 |
| 4,506,453 | 3/1985 | Shirley, Jr. et al. | 264/7 |
| 4,507,335 | 3/1985 | Mathur | 427/215 |

FOREIGN PATENT DOCUMENTS 3024292 6/1980 Fed. Rep. of Germany .

OTHER PUBLICATIONS

Condensed Chemical Dictionary, 10th ed. p. 137.

_Primary Examiner_—Jan H. Silbaugh
_Assistant Examiner_—Mary Lynn Fertig

[57] ABSTRACT

A prilling apparatus and process for producing seed material for size enlargement processes such as a granulation process for bisphenol. The apparatus includes a fluidized bed system with a spray header therein for producing spray droplets of material in a gaseous stream such as nitrogen to form prills of less than about 1 mm diameter.

2 Claims, 2 Drawing Sheets 4,935,173

PROCESS FOR PRODUCING PRILLS

CROSS REFERENCE TO RELATED APPLICATION

This is a divisional of application Ser. No. 005,507, filed Jan. 20, 1987, now U.S. Pat. No. 4,793,783.

BACKGROUND OF THE INVENTION

This invention relates to an apparatus and process for producing prills useful as seed material for size enlargement processes such as for a bisphenol granulation process.

Heretofore, seed material for size enlargement processes, i.e. granulation processes, has been formed by milling or crushing product formed in the various size enlargement processes. The crushing process for producing seed material generates high levels of dust and is inefficient. For example, as much as 60 percent of the material used in the crushing process may be ground too finely for it to be useful in various granulation processes. Additionally, these fines must be removed from the desired size particles.

Therefore, it is desired to provide a novel seed generation device to replace the crushing or milling step in processes requiring seed material.

SUMMARY OF THE INVENTION

One aspect of the present invention is a prilling apparatus for producing seed material for further size enlargement processes. The apparatus includes a housing defining a chamber containing a fluidized bed of particulate material and an inlet and an outlet for a fluidizing gas stream flow therethrough, a spray header disposed in the housing such that a multiplicity of fountain-like fluid streams of material in the molten state are sprayed in a spraying zone of the chamber above the fluidized bed at an angle such that the individual streams are not contacting each other or the internal surfaces of the chamber, and an outlet for product to flow from the chamber.

Another aspect of the invention is a process for producing prills by passing a fluidizing gas stream through a fluidized bed and contacting a molten material with the fluidizing gas stream such that prills are formed.

DETAILED DESCRIPTION OF THE PREFERRED EMBODIMENTS

Figure 1:
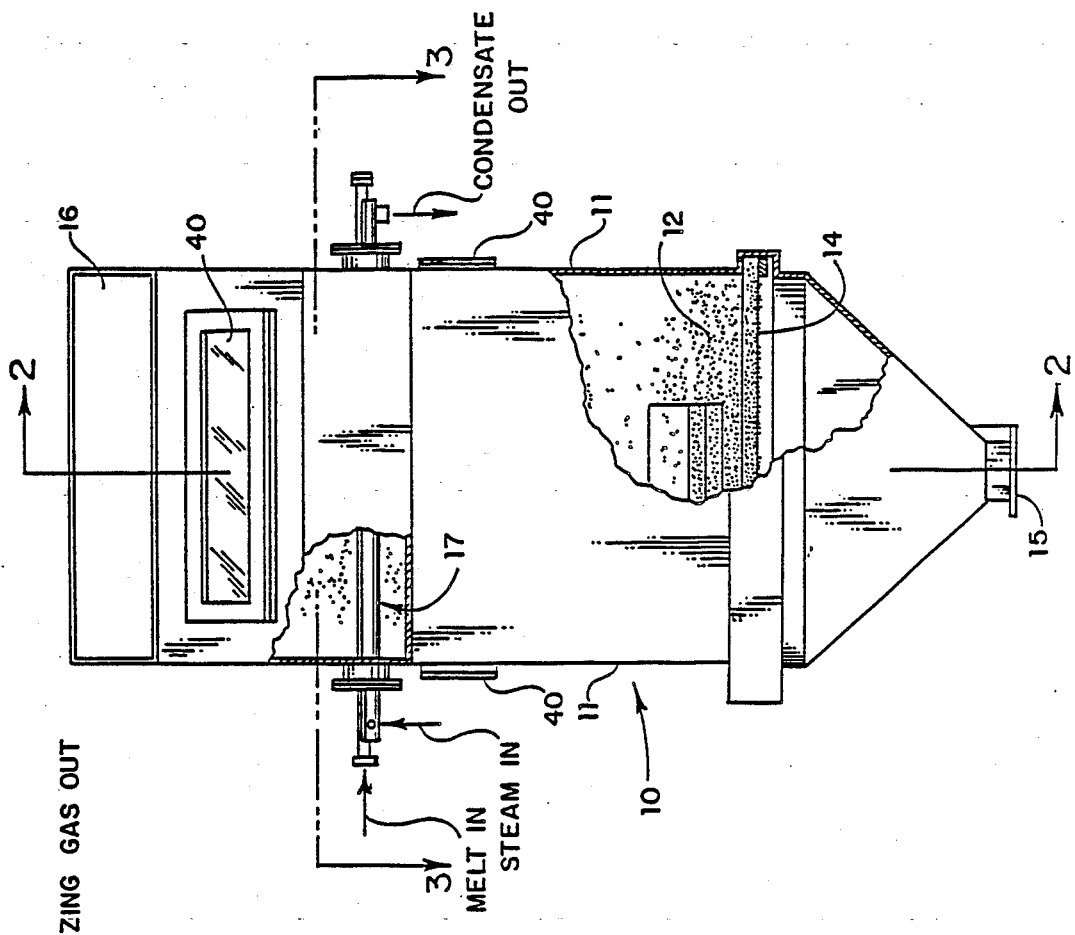
FIG. 1 is a front view of the prilling apparatus of the present invention.
Figure 2:
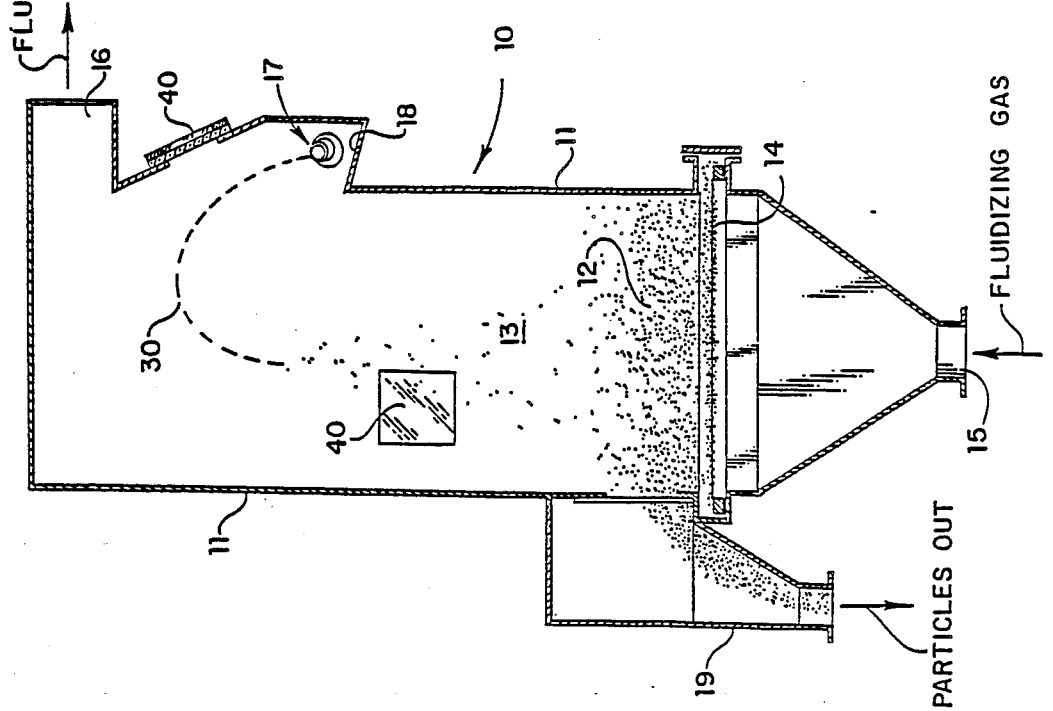
FIG. 2 is a cross-section view of the prilling apparatus of FIG. 1 taken along the line 2—2.
Figure 3:
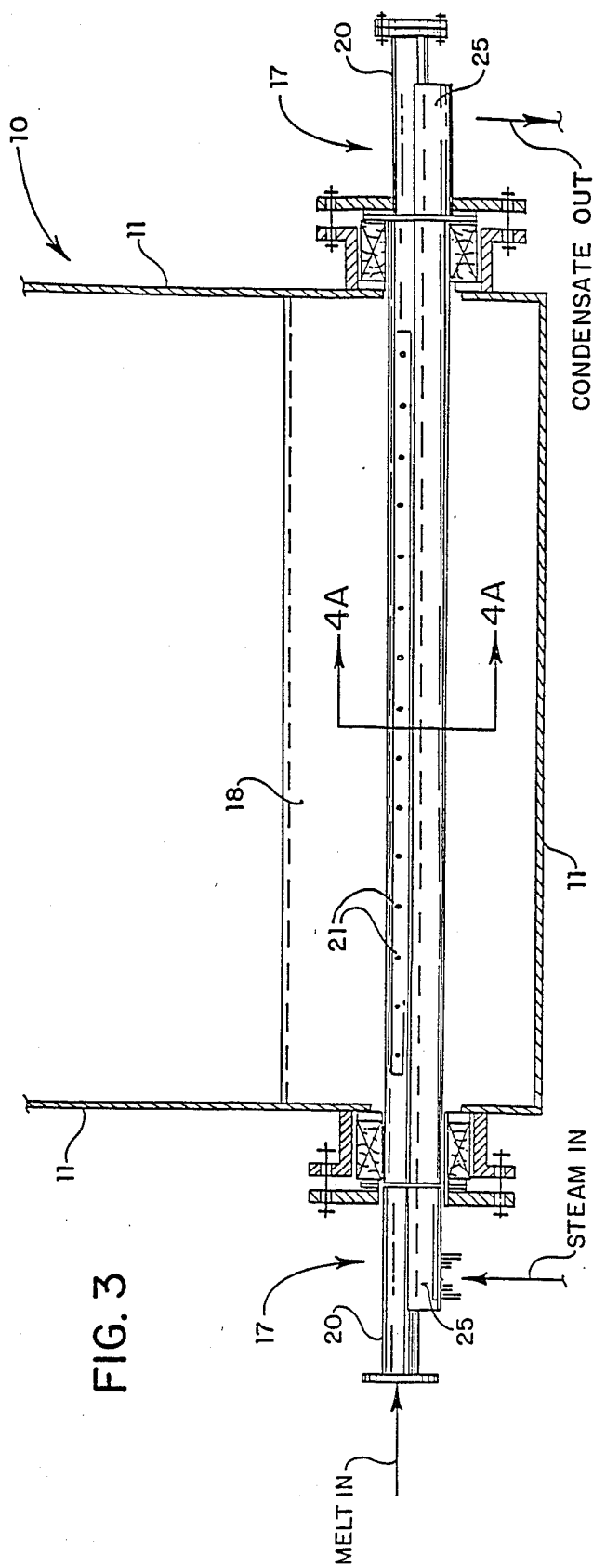
FIG. 3 is a top view of the prilling apparatus of FIG. 1 taken along the line 3—3.

With reference to FIGS. 1–3, a prilling apparatus, generally indicated by the numeral 10, is shown with a housing 11 containing a particulate material 12 initially charged into a chamber 13 for providing a fluidized bed. A bed support member, for example a foraminous plate or screen 14 is used to hold the material 12 in the chamber 13 providing a fluidizing zone above the screen. An inlet 15 and outlet 16 is provided in the apparatus 10 for passing a fluidizing gas stream through the chamber 13 for fluidizing the material 12. The fluidizing gas stream is also used for cooling molten streams 30 which in turn, forms prills. The streams 30 are introduced into the chamber 13 using a spray header assembly 17 disposed in a spraying zone in the chamber 13.

The spray header assembly 17 is disposed in the chamber 13 for spraying the molten stream 30 of feed material at such an angle from horizontal so that the droplets of molten material in stream 30 first travel in a generally upwardly direction and then in a generally downwardly direction, allowing maximum contact time with the cool fluidizing gas stream before the droplets reach the fluidized bed at near the bottom of the apparatus. A side view of an individual spray stream would be a fountain-like stream in an inverted "U-shape". The spray header 17 is disposed within the housing 11 on a ledge or shoulder portion 18 in the inside of the sidewalls of housing 11. The arrangement of the spray header assembly 17 on shoulder portion 18 substantially eliminates any disturbance of the spray streams 30 at the point of discharge from the header orifices 21 by the gas flow stream.

Figure 4B:
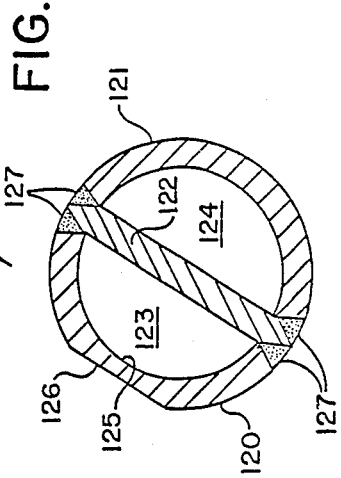
FIG. 4B is a cross-section view of another embodiment of the spray header system of the present invention.
Figure 4A:
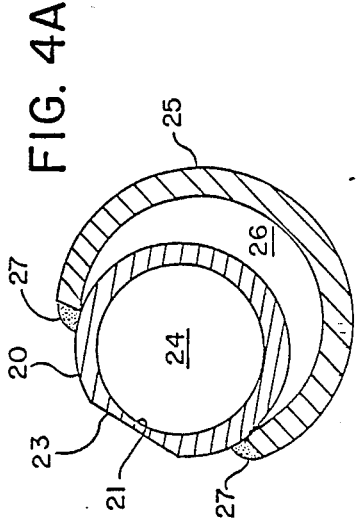
FIG. 4A is a cross-section view of the spray header system shown in FIG. 3 and taken along the line 4A—4A.

The spray header assembly 17, more clearly shown in FIG. 4A, includes an elongated molten feed pipe member 20 having a plurality of orifices 21 disposed on a flat surface 23 of the pipe member 20. A space 24 of pipe 20 is used for feeding molten material to the orifices 21. The spray assembly 17 includes a heating fluid feed jacket pipe member 25 mounted on the molten feed pipe 20 forming a space 26 for feeding a heating fluid therethrough. The pipe member 25 may be attached to the pipe member 20 by any means such as welding at points 27. Preferably, steam is used as the heating fluid in space 26 for maintaining the molten feed in space 24 in a molten state as the feed passes through the orifices 21. The flat surface 23 on pipe 20 is not critical in the present invention, however, it is preferred to provide a flat surface 23 along the entire longitudinal length of the pipe 20 for ease of drilling the orifices 21 on the pipe 20. The spray header assembly 17 shown in FIG. 4A can be easily manufactured, for example, by welding a first pipe member into a second pipe member having a larger diameter than the first pipe member and having a portion cut out to accommodate the first pipe member. The second pipe member is disposed in a generally annularly about the first pipe member and the first pipe member is within the inside diameter of the second pipe member in a non-coaxial manner.

In FIG. 4B, there is shown another embodiment of the spray header assembly of the present invention, generally indicated by numeral 117, including a molten feed pipe member portion 120 and a heating fluid feed pipe member portion 121 with a flat plate or baffle 122 forming a space 123 and a space 124. The pipe portion 120 and 121 and the baffle 122 are attached together by any means such as welding 127. The pipe member portion 120 contains a plurality of orifices 125 on flat portion 126. Space 123 is used for feeding molten material to orifices 125. Space 124 is used for feeding heating fluid such as steam therethrough such that the molten feed in space 123 is maintained in a molten state. The orifices 125 are provided on a flat surface 126 along the longitudinal length of pipe portion 120. The spray header assembly in FIG. 4B can be easily manufactured, for example, by cutting a pipe member in half and welding a flat plate between the two pipe member halves along the longitudinal length of the two pipe member halves.

The spray header assembly 17 advantageously, provides a steam heating design that eliminates the need for a cumbersome steam tracing or jacketing system of the prior art.

A discharge chute 19 is used to remove product from the housing 11. Windows 40 are provided in the housing 11 for visual inspection of the spray streams inside the housing chamber 13.

The present invention will be described herein in detail with reference to production of bisphenols, however, it is understood that other materials which produce a solids free melt can be used in the invention. For example, materials such as bisphenols normally are substantially solid at ambient temperatures but can be reduced to a sprayable liquid state by melting and can be returned to the solid state by cooling below the melt temperature.

The fluidizing gas stream used in the process of producing bisphenol prills is nitrogen. Nitrogen is used to reduce color changes in the product and reduce the chances of creating an explosive atmosphere within the apparatus. Of course, other cooling and fluidizing mediums can be used which are nonreactive with the product that is being prilled. For example, other inert atmospheres can be used. Air can also be used when the product being prilled is not reactive with air and when a relatively inexpensive and readily available cooling and fluidizing medium is desired. Recirculation of the fluidizing gas stream is also possible for example, by adding dust removal and cooling equipment to the present system.

In carrying out one embodiment of the process of the present invention, with reference to FIG. 2, a nitrogen stream is passed through the chamber 13, entering through the inlet 15 and exiting through the outlet 16 to maintain the bed of particulate material 12 in a fluidized condition. Molten feed of the material desired to be prilled, i.e. the bisphenol, is fed through the steam heated spray header assembly 17. Molten feed spray streams 30 are produced as the molten material exits the orifices 21 of pipe 20.

The spray header pressure, orifice size and spray angle are adjusted to produce a droplet size and a spray pattern such that the molten spray is projected upwardly and slightly concurrent with the fluidizing gas stream, toward the topmost portion of the chamber without contacting the internal surfaces of the housing and such that the droplets of molten material gently fall back downwardly and generally countercurrent to the gas stream and into the fluidized bed. As the droplets are cooled by the gas stream, the droplets solidify into a prill or bead form. Agitation of the fluidized bed by the nitrogen stream helps to keep the beads from sticking together.

The spray streams 30 are directed up at such an angle of maximize the contact time between the spray droplets and the nitrogen flow. Maximization of the contact time of the droplets and nitrogen in turn maximizes the heat transfer between the droplets and nitrogen flow. This reduces the required nitrogen flow. The spray header preferably produces a uniform substantially planar or flat spray pattern as the spray streams leave the orifices 21. In other words, the spray streams do not cross each other or diverge from one another when viewed in cross-section as the streams leave the orifice 21. The header evenly distributes the substantially equally spaced spray streams over the substantially entire gaseous flow area which keeps the droplets from hitting the sides of the chamber. This, in turn, prevents the buildup of molten material on the internal surfaces of the housing. In addition, stream collision problems are prevented which, in turn, prevents agglomeration of the resultant prills. An irregular or nonlinear spray pattern such as a conical spray pattern created by a nozzle would cause the aforementioned problems. Because of the resultant spray pattern of the present invention, the spray header system requires a much smaller cross-sectional area for the prill chamber than conventional prilling apparatuses.

It is preferred to keep the spray header at a temperature of about 2° C. to about 10° C. above the melting point of the material being prilled. Operation of the header at temperatures below this range may produce an irregular spray pattern and plugging of the holes in the spray header. Operation of the header above this temperature range allows molten droplets to reach the fluidized bed and create agglomerations.

The orifice size in the spray header preferably are from about 0.005 to about 0.07 inch in diameter. The orifice hole size in connection with the spray header pressure determines the final product prill size. The spray header pressure preferably is adjusted unconditionally to produce the optimum spray height. The spray header orifice size can be adjusted to set final product size.

The minimum nitrogen flow used is determined by the fluidized bed requirements. The maximum nitrogen flow is reached when beads start being carried overhead in the nitrogen exit. Examples of nitrogen flows used have ranged from about 4000 SCFM to about 6000 SCFM in a fluidized bed having dimensions of about 3.5 feet by 4 feet.

During operation of the present process using bisphenol, less than about 1% dust is generated and less than about 5% agglomerations of beads is produced. However, the results of dust and agglomerations may vary with use of different feed materials.

The apparatus and process of the present invention can be used to produce bisphenol seed material having a particle size of less than about 1 mm diameter for size enlargement processes. For example, a size enlargement process in which the present invention is particularly useful is described in U.S. patent application No. 005,504, entitled "Production of Granular Bisphenols", filed Jan. 20, 1987, under the names Kenneth P. McDonald and Arthur Ray Shirley, incorporated herein by reference. This process for producing bisphenol granules includes feeding a bisphenol seed material into a rotary granulation drum enclosed in a gastight housing and spraying molten bisphenol onto the seed material in the presence of an inert gaseous atmosphere such as nitrogen.

The apparatus and process of the present invention is also useful for producing prills having a particle size of less than about 1 mm diameter and as such can be an alternate to conventional prilling towers or other bead forming processes where a particle size of less than about 1 mm diameter is desired.

EXAMPLE

A prilling apparatus having the following dimensions was used to form seed material of bisphenol:

The height was 10 feet, the width was 4 feet and the depth was about 3.5 feet. About 4 feet from the bottom of the apparatus there was installed a spray header containing 72 holes with 0.0135 inch diameter. The holes were at about a 75 degree angle from horizontal.

A melt at 230 lb/hr and 8 psig was passed through the header. Air at about 5000 SCFM was passed from the bottom of the apparatus through the spray droplets.

The prills formed were 0.75 mm in size.

What is claimed is:

1. A process for producing prills comprising
   (a) providing a housing with a top, bottom and side walls defining interiorly thereof a chamber;
   (b) providing a bed support member disposed within the housing and dividing the chamber into a fluidizing zone thereabove and fluidizing gas plenum therebeneath; the chamber including a spraying zone above the fluidizing zone;
   (c) providing a spray means including an elongated tubular header with a plurality of orifices therein;
   (d) passing a cooling fluidizing gas into the fluidizing gas plenum to pass through the bed support member into the fluidizing zone to fluidize a bed of prills formed in the chamber such that the prills are agitated sufficiently to prevent agglomeration of the prills;
   (e) spraying a spray stream of molten material through the spray means into the chamber in the spraying zone above the fluidizing zone at an upward angle such that individual streams from the plurality of orifices do not contact each other or internal surfaces of the chamber, the spray means disposed near at least one side wall of the chamber such that the spray is diverted into the cooling fluidizing gas passing from the fluidizing zone through the spraying zone and such that spray droplets formed fall toward the fluidized bed of the chamber for a sufficient time to form prills upon contact with the fluidized bed;
   (f) removing the fluidizing gas passing through the spraying zone; and
   (g) removing the prills from the fluidized bed.

2. The process of claim 1 wherein the spray is directed toward the topmost portion of the chamber first in a substantially concurrent manner to the fluidizing gas stream and then such that the spray droplets formed fall substantially countercurrent to the fluidizing gas stream toward the fluidized bed without contacting the internal surfaces of the chamber.

* * * * *